United States Patent
Leonard et al.

(10) Patent No.: US 7,997,268 B1
(45) Date of Patent: Aug. 16, 2011

(54) VETERINARY ANESTHESIA MONITOR SYSTEM

(75) Inventors: Robert Dean Leonard, Fallbrook, CA (US); David Robert Wilson, Platteville, CO (US)

(73) Assignee: Intellivet Anesthesia Equipment, LLC, Las Vegas, NV (US)

( * ) Notice: Subject to any disclaimer, the term of this patent is extended or adjusted under 35 U.S.C. 154(b) by 804 days.

(21) Appl. No.: 11/015,412

(22) Filed: Dec. 17, 2004

Related U.S. Application Data

(60) Provisional application No. 60/530,689, filed on Dec. 17, 2003.

(51) Int. Cl.
*A61M 15/00* (2006.01)
*A61M 16/00* (2006.01)
*F16K 31/02* (2006.01)

(52) U.S. Cl. ......... 128/203.12; 128/203.14; 128/203.25; 128/204.22

(58) Field of Classification Search ............. 128/203.12, 128/203.14, 203.25, 204.22
See application file for complete search history.

(56) References Cited

U.S. PATENT DOCUMENTS

| | | | | |
|---|---|---|---|---|
| 4,150,670 A | * | 4/1979 | Jewett et al. | 128/204.22 |
| 4,986,268 A | * | 1/1991 | Tehrani | 128/204.22 |
| 5,094,235 A | * | 3/1992 | Westenskow et al. | 128/204.22 |
| 5,243,973 A | * | 9/1993 | Falb et al. | 128/203.27 |
| 5,282,473 A | * | 2/1994 | Braig et al. | 600/532 |
| 5,320,093 A | * | 6/1994 | Raemer | 128/203.12 |
| 5,778,874 A | * | 7/1998 | Maguire et al. | 128/204.22 |
| 5,824,885 A | | 10/1998 | Lekholm | |
| 5,967,141 A | * | 10/1999 | Heinonen | 128/203.12 |
| 6,289,891 B1 | | 9/2001 | Cewers | |
| 6,333,512 B1 | * | 12/2001 | Wirthlin | 250/577 |
| 6,448,791 B1 | | 9/2002 | Cewers | |

* cited by examiner

*Primary Examiner* — Patricia M Bianco
*Assistant Examiner* — Nihir Patel
(74) *Attorney, Agent, or Firm* — Craig R. Miles; CR Miles, P.C.

(57) ABSTRACT

A veterinary anesthesia monitor system useful in establishing, maintaining, and reporting upon the anesthesia gas mixture delivered to or exhaled by a patient.

13 Claims, 6 Drawing Sheets

VETERINARY ANESTHESIA MONITOR SYSTEM

This application claims the benefit under 35 U.S.C. §119 (e) of U.S. provisional patent application No. 60/530,689, filed Dec. 17, 2003, hereby incorporated by reference herein.

I. BACKGROUND

An anesthesia device which monitors the amount of anesthetic held for vaporization and the amount of anesthetic and carbon dioxide in the mixture of gases in the circular re-breathing system.

During veterinary or human surgical procedures, a conventional anesthesia device entrains an amount of anesthetic into a mixture of gases utilizing an anesthetic vaporizer. The anesthetic entrained in the mixture of gases can be delivered for inhalation by a patient in a circular re-breathing system. The depth of general anesthesia depends on the partial pressure (or gas fraction) exerted by the inhalation anesthetic (or inhalation agent) on the patient's brain. This brain partial pressure of the inhalation anesthetic depends on arterial blood partial pressure of the inhalation anesthetic which depends on the alveolar partial pressure of the inhalation agent which in turn depends on the partial pressure of the inhalation anesthetic in the inhaled mixture of gases. To change the partial pressure exerted by the inhalation anesthetic on the patient's brain, the partial pressure of the anesthetic or inhalation agent is adjusted in the inhaled mixture of gases. The partial pressure of the inhalation anesthetic is equal the mole fraction of the inhalation anesthetic times the total pressure of the inhalation gases.

An important concept in comparing inhalational anesthetics is their measure of potency called the minimum alveolar concentration (MAC). It is defined as the concentration of a particular inhalational anesthetic at one atmosphere pressure in which 50 percent of patients do not move in response to a skin incision. Therefore, the potencies (as well as side effects at similar potencies) of different inhalational anesthetics can be compared; so can combinations of inhalation anesthetics. In general, a half MAC of each of two inhalational anesthetics is equivalent to one MAC of either. The MAC of inhaled anesthetics in one hundred percent oxygen, varies:

| Halothane | 0.74 percent |
| Enflurane | 1.68 percent |
| Isoflurane | 1.15 percent |
| Desflurane | 6.30 percent |
| Sevflurane | 2.00 percent |

Conventional veterinary inhalation anesthesia utilizes an anesthesia device that incorporates an oxygen flow meter, an anesthetic vaporizer, and circular re-breathing system with carbon dioxide absorption. As but one example, Isoflurane inhalation utilizing conventional anesthesia devices can provide general anesthesia for a variety of animal species, including without limitation, dogs, cats, birds, mice, rats, guinea pigs, and macaques.

Often a fast acting but short lived sedative is administered to the animal by injection and an endotracheal tube is placed in the animal's windpipe through which oxygen and the inhalation anesthetic are delivered. For isoflurane anesthetic induction, the oxygen flow rate is typically calculated at 100 milliliters per kilogram of body weight per minute and the anesthetic vaporizer set at between three percent to about four percent. Isoflurane anesthetic maintenance is typically achieved by delivery of a minimum oxygen flow rate of about 500 milliliters per minute for animals of less than 50 pounds body weight and an additional 100 milliters per minute for each additional ten pounds of body weight up to 100 pounds of body weight with the vaporizer set to deliver between 1.5 percent and 2.0 percent Isofurane.

A significant problem with conventional anesthetic delivery devices and procedures can be that the anesthetic vaporizer may not be properly readjusted after delivery of anesthetic during the induction period. With regard to both humans and animals, patients have been inadvertently overdosed during anesthetic induction and during subsequent maintenance anesthesia. See for example, Patermann, B., Buzello, S., Dück, M., Paul, M. and Kampe, S., "Accidental Tenfold Overdose of Propofol in a Six-month Old Infant Undergoing Elective Craniosynostosis Repair" Anaesthesia 59 (9), 912-914 (2004). Even during resuscitation attempts oxygen delivered from the anesthesia machine can be contaminated with inhalation anesthetic because the vaporizer has been accidentally been left on the full ON position. See for example, Randall, B., and Corbett, B., "Fatal Halothane Poisoning During Anesthesia with Other Agents" Journal of Forensic Sciences, Vol. 27, Issue 1, (January 1982). With respect to animals, with Irish Wolfhounds and Rottwieler breeds mainly in mind, cases have occurred where dogs have died under maintenance anaesthesia and it is considered that these breeds are sensitive and may not require the dosage its weight might indicate, as such induction and maintenance anesthesia may require more reliable monitoring of general anesthesia.

Another significant problem with conventional anesthesia delivery devices and procedures can be that visual observation of the amount of anesthetic in the anesthetic vaporizer can be required to ensure that the proper amount of anesthetic is held for delivery by the anesthetic vaporizer to the inhalation circuit. By periodic observation and comparison of the amount of anesthetic remaining in the anesthetic vaporizer to a mark inscribed on a viewing aperture an estimate the amount of anesthetic delivered can be made for certain models of anesthetic vaporizers.

However, visualization to estimate the amount of anesthetic in the anesthetic vaporizer and comparison to the prior estimated amount of anesthetic in anesthetic vaporizer to determine the amount of anesthetic delivered from the anesthetic vaporizer may not yield consistent delivery of anesthetic from the anesthetic vaporizer or the proper partial pressure of the inhalant anesthetic delivered to the patient. Inconsistent, inaccurate, or undesired delivery rates of anesthetic from the anesthetic vaporizer or partial pressures of anesthetic inhalants delivered to the patient can result from the failure of or inconsistency of the operator. In certain instances, the operator may simply become distracted from visualizing, or forget to visualize, the amount of anesthetic in the anesthetic vaporizer. Alternately, anesthetic visualization may occur less frequently than required, or the elapse of time between visualization events may vary to a greater degree than necessary to generate a required, predetermined, consistent, or desired delivery of anesthetic from the anesthetic vaporizer or partial pressure of anesthetic inhalant delivered to the patient. Also, visualization by the operator may simply be in error as to the actual amount of anesthetic in the anesthetic vaporizer.

In addition, anesthetic visualization and calibration of the anesthetic vaporizer can be complicated by the numerous different anesthetics which may be delivered to patients, each of which may have unique anesthetic characteristics (density, boiling point, vaporization rate, or the like). As such, vaporizers may be configured differently or calibrated differently for the delivery of each of the various anesthetics.

In other instances, conventional vaporizers may be poorly designed contributing to operator error, fail to operate, operate out of calibration, operate inconsistently, or operate in an other undesired manner, making estimation of anesthetic delivery less consistent, less precise, or in some cases not possible at all. See for example, Buettner, A. U., "Failure of Vaporizer Interlock Mechanism." Anaesthesia & Intensive Care. 2000; 28:451-2.

Another significant problem with conventional anesthesia delivery devices and methods can be that only visualization or dependence upon calibration of the anesthetic vaporizer may used to estimate the amount of anesthetic delivered from the anesthetic vaporizer to the re-breathing system. As discussed above, reliance on calibration or visualization to estimate the partial pressure of anesthetic in the re-breathing system may not provide information as to the actual condition of the gas mixture inhaled by the patient, or the subsequent condition of the gas mixture exhaled by the patient.

Upon exhalation by the patient the remaining amount of anesthetic gas and the exhaled mixture of gases can be transferred to an absorber to remove carbon dioxide gas (CO2) with a CO2 absorbent. The absorbent, which initially absorbs substantially all the CO2, gradually becomes saturated until the absorbent no longer retains CO2 and levels of CO2 in the re-breathing system can rise to levels harmful to the patient. The absorbent typically contains an indicator which changes color prior to saturation with CO2, however, the saturation point at which the indicator changes color can vary. As such, color change can be unreliable and harmful CO2 levels can build up in the re-breathing circuit of conventional anesthesia device of which the operator can be unaware resulting in harm to the patient.

With respect to the above-mentioned problems associated with conventional anesthesia devices, methods of anesthesia delivery and monitoring of inhalation anesthesia, the present invention addresses each.

II. SUMMARY OF THE INVENTION

Accordingly, a broad object of embodiments of the invention can be to provide an anesthesia device, whether for humans or for animals, which monitors the mixture of gases in the re-breathing circuit.

One aspect of this broad object of the invention can be to provide a sensor which monitors the amount of anesthetic available in the vaporizer for entrainment in the flow of gas(es) delivered thereto. During general anesthesia change in anesthetic amount in the anesthetic source can thereby be monitored independent of conventional visualization or vaporizer calibration procedures.

A further aspect of this broad object of the invention can be to provide a sensor which monitors the amount of carbon dioxide in the re-breathing circuit, or independently the inhalation circuit or the exhalation circuit, or both. Monitoring the amount (whether as a percent, concentration, or partial pressure) of carbon dioxide can provide additional information to control the mixture of gases in the re-breathing circuit or provide indicia to time replacement of carbon dioxide absorbent.

Another aspect of this broad object of the invention can be to provide a sensor which monitors the type or kind of anesthetic in the re-breathing circuit, the partial pressure of anesthetic in the re-breathing circuit, or the flow rate of the gas(es) entraining the anesthetic.

Monitoring the type or kind of anesthetic in the re-breathing circuit avoids delivery of an improper anesthetic to the patient in the first instance and also provides retrieval of additional data (which may be stored in a computer memory) to control manually or automatically the temperature of the anesthetic in the anesthetic source, the flow rate of gas(es) to the anesthetic source to entrain anesthetic for delivery to the patient, or other general anesthesia parameters to induce and maintain patient anesthesia.

Another aspect of this broad object of the invention can be to provide a controller which processes information from each sensor to provide outputs in the form of visual or audible indicia to the operator or as feedback to control various functions of the anesthesia device, such as flow rate of gas(es) to the anesthetic source, the amount of anesthetic entrained in the flow of gas(es), the partial pressures of gases in the inhalation circuit, the partial pressure of gases in the exhalation circuit, temperature of the anesthetic.

Another aspect of this broad object of the invention can be to provide additional computer hardware which provides storage and retrieval of data and programmed or programmable elements relating to anesthesia profiles for various anesthetics and inhalation anesthesia applications. The programmed or programmable elements can further provide a program which allows tracking of the anesthesia profiles in conjunction with monitoring of the conditions in the re-breathing circuit to assure that the desired anesthesia profile is being correctly implemented.

Naturally, other objects of the invention are disclosed throughout the description, the claims, and the drawings.

III. BRIEF DESCRIPTION OF THE DRAWINGS

IV. DETAILED DESCRIPTION OF THE PREFERRED EMBODIMENTS

In general, an anesthesia device which monitors the amount of anesthetic held for vaporization and characteristics of the mixture of gases in the circular re-breathing system. Specifically, a veterinary anesthesia device which can monitor the amount of anesthetic held in the vaporizer and which can monitor the amount of anesthetic and amount of carbon dioxide in the circular re-breathing system.

Figure 1:
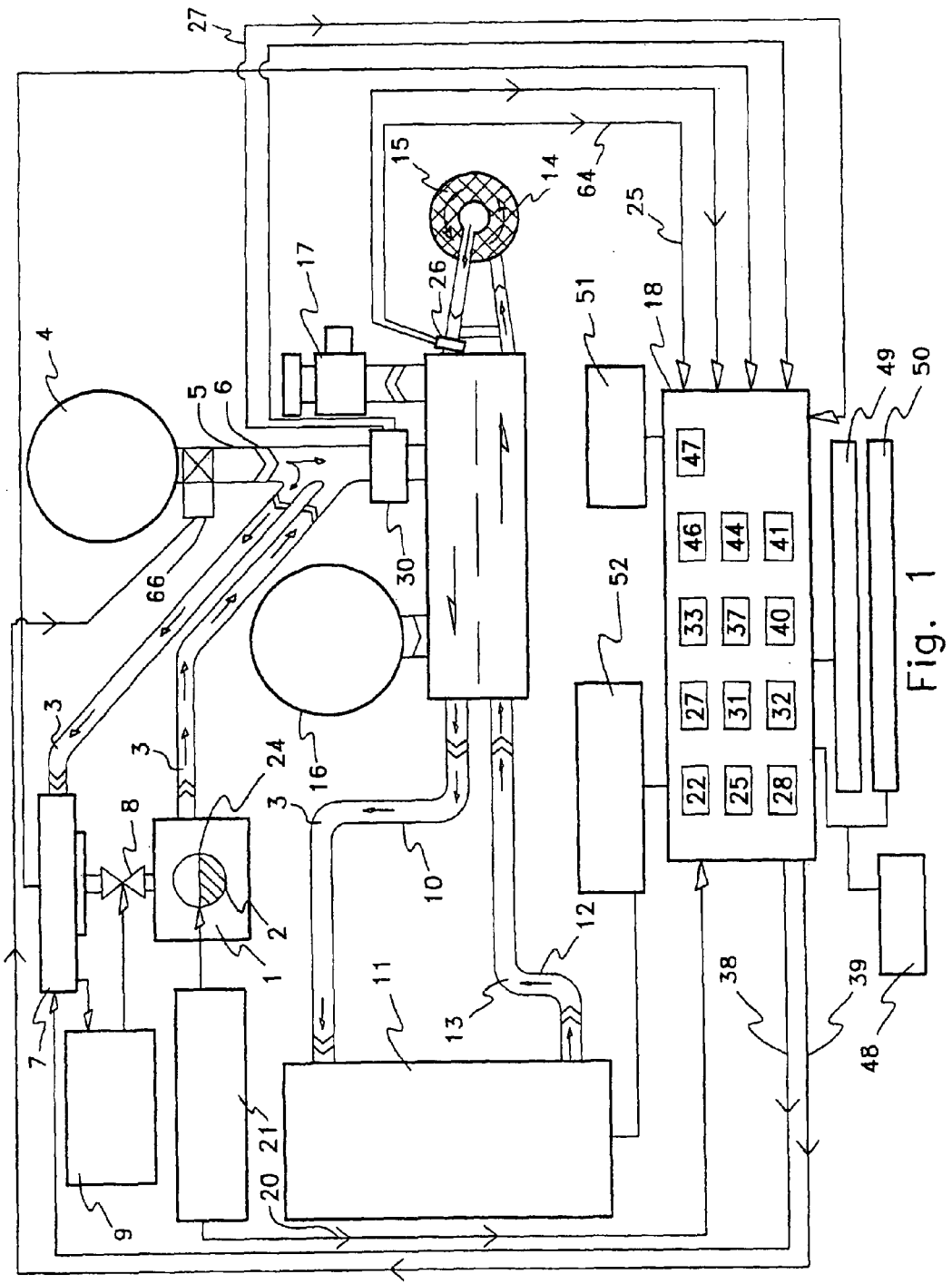
FIG. 1 shows a block diagram of a particular embodiment of the anesthesia device invention.

First referring primarily to FIG. 1, an embodiment of the anesthesia device in accordance with the invention provides an anesthetic source (1) in which an amount of anesthetic (2) is established. The anesthetic source (1) entrains an amount of anesthetic (2), such as, Halothane, Enflurane, Isoflurane, Desflurane, Sevflurane, or the like, in a flow of gases (3). The flow of gases (3) can be gas flow generator (4) which without limitation can comprise a compressed gas cylinder coupled to a gas pressure regulator (5) and a gas flow meter (6). The gas flow generator can establish a flow of oxygen, or other mixture of gases having selected partial pressures, into the anesthetic source (1). The anesthetic source can further comprise a gas flow regulation element (7) having a closure (8) operated by an actuator (9). The flow of gases (3) in which an amount of anesthetic (2) is entrained passes into the inhalation circuit (10) and to be delivered to the patient (11). A portion of the anesthetic may not enter the patient's blood stream and may be exhaled into the exhalation circuit (12). The exhaled mixture of gases (13) and the remaining entrained anesthetic (2) may be transferred to a carbon dioxide absorber (14) and the carbon dioxide in the exhaled mixture of gases (13) may be transferred to a carbon dioxide absorbent (15) contained within the carbon dioxide absorber (14). The resulting mixture of gases can be returned to the inhalation circuit (10) and supplemented with an additional amount of anesthetic (2) from the anesthetic source or oxygen (or other partial pressures of gases) from the gas flow generator (4) as necessary to maintain inhalation anesthesia. A flexible breathing bag (16) accommodates the respiratory volume of the patient (11). A pressure relief valve (17) can be provided for release of the mixture of gases from the inhalation and exhalation circuits (10) (12) to maintain the desired gas pressure within the re-breathing circuit.

Figure 2:
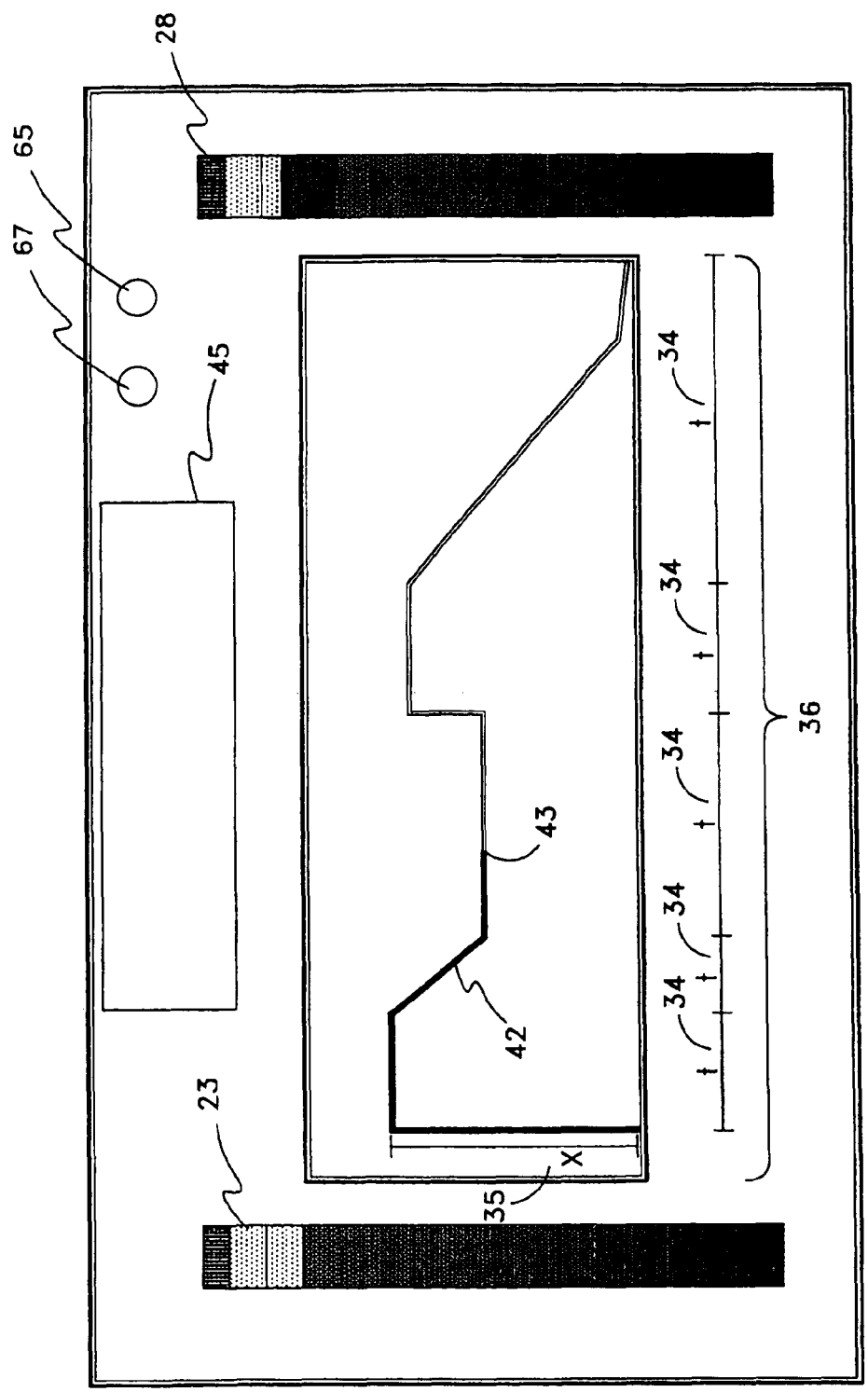
FIG. 2 shows a non-limiting example of indicators and visual indicia which can be generated in conjunction with monitoring various operating conditions of the anesthesia device.

Now referring to FIGS. 1 and 2, certain embodiments of the invention can provide a controller (18) which can be pre-programmed, through firmware, software, subroutines or data to provide a variety of functions relating to the operation of the anesthesia device and monitoring of functions performed by the anesthesia device. As to certain embodiments of the invention, the controller (18) can receive and process a first signal (20) generated by a first sensor (21) utilizing a first signal processor (22) to provide one or more anesthetic level indicia (23) relating to the level (24) of anesthetic (2) in the anesthetic source (1). As to other embodiments of the invention the controller (18) can receive and process a second signal (25) from a second sensor (26) utilizing a second signal processor (27) to provide one or more carbon dioxide level indicia (28) relating to the percent carbon dioxide ("CO2"), partial pressure of CO2, concentration of CO2, or other measure of CO2 in the inhalation circuit (10) or the exhalation circuit (13), or both, depending on the location of the second sensor (26). As to certain embodiments of the invention the controller (18) can receive and process a third signal (29) from a third sensor (30) utilizing a third signal processor (31) relating to type or kind of anesthetic, percent anesthetic, partial pressure of anesthetic, or concentration of anesthetic delivered to the inhalation circuit (10) or delivered to the patient (11).

As to certain other embodiments of the invention the controller (18) an anesthesia profile generator (32) can establish an anesthesia profile (33). As a non-limiting example, a basic anesthesia profile (33) can establish for each time period (t) (34) of the anesthesia event the amount of oxygen (x) (35) or partial pressure of oxygen, in the mixture of gases delivered to the inhalation circuit (10) for inhalation by the patient (11) (the delivery of anesthetic from the anesthetic source (1) being held substantially constant in this example). The anesthesia profile (33) can be generated as and anesthesia profile display (36) utilizing a anesthetic profile display generator (37) of the controller (18). As to more complex embodiments of the invention, the anesthesia profile (33) may establish for each time period (26) of the anesthesia event the amount of anesthetic, the amount of oxygen, or the amount of CO2 in the inhalation circuit (10). Pre-programmed anesthesia profiles (33) (for a veterinary anesthesia device as a non-limiting example) for "small animal", "medium animal", or "large animal", or a drill down menu of anesthetic delivery profiles "small animal"/"dog"/"Pomeranian" can be generated.

The signals (20) (23) (25) received and processed by the controller (18) can be used to generate a gas flow regulation signal (38) to the gas flow regulation actuator (7) to adjust the closure (8) to entrain the proper amount of anesthetic (2) into the flow of gases (3), to generate a gas flow metering signal (39) to adjust the gas flow meter to regulate the flow, pressure, or partial pressures of the mixture of gases in the inhalation circuit (10) such that actual delivery of anesthetic (2), oxygen, or other partial pressures of gases to the inhalation circuit (10) corresponds to the anesthesia profile (33). In certain embodiments of the invention, the signals (20) (23) (25) can further be processed by an anesthesia profile tracker element (40) that compares the actual conditions in the inhalation circuit (10) to the anesthesia profile (30) initially established. The control unit can further include an anesthesia profile tracker indicator generator (41) which generates an anesthesia profile tracker (42) which indicates the time elapsed (43) of the anesthesia profile (33) and an anesthesia profile alarm element (44) which can generate audible or visual indicia (45) when the anesthesia profile tracker element (40) assesses a deviation from the anesthesia profile (33). A non-limiting example of an anesthesia profile (19) and anesthesia profile tracker element (30) are shown by FIG. 2.

Selectably adjustable anesthesia profiles (33) can be programmed with the controller (18) utilizing a time duration selection element (46) to establish the time period (t) (34) and a gas partial pressure selection element (47) to establish the amount of oxygen (x) (35) (or other mixture of gases) in the inhalation circuit (10) during each time period (t) (34). As such, the operator can program anesthesia profiles having a plurality of time periods (34). Selectably adjustable anesthesia profiles (33) can include a simple anesthesia profile (in which anesthetic delivery is held substantially constant) such as "oxygen (x) 200 milliliters per minute during a first three minute time period (t), and oxygen (x) 500 milliliters per minute during second 60 minute time period" or more complex anesthesia profiles (33) in which a partial pressure of gases (x) is programmed in a plurality of time periods (t) (34).

Again referring to FIG. 1, the invention can further include a control unit interface (48) to allow the user to program or select various anesthesia profiles, information display, alarm, sensor, or actuator parameters perhaps through drill down menus, voice command, push button switches, touch screen display, or any means by which a user can input data or select parameters for operation of an embodiment. As to certain embodiments of an invention the interface may be a hand operated interface (49) or a foot operated interface (50) which may provide "hands free" interface with the control unit (18) under certain circumstances.

With respect to certain embodiments, the control unit (18) can further include data input elements (51). Such elements may directly or indirectly receive information from equipment such as electroencephalograph or other physiological monitor (52) responsive to the patient (11). These elements may be used as control functions for any of the anesthetic systems described in this disclosure, In embodiments, the data input elements (36) in conjunction with the control unit (17) can be used at this time, control or modify anesthetic delivery to the patient (7) or time, terminate, modify or otherwise control anesthetic delivery profiles (18). Out put data (38) from the various sensors may be recorded for historical or analytical purposes.

The controller (18) can be configured in a variety of ways to achieve the various operation parameters of the invention, certain embodiments of control unit in accordance with the invention can include:

a. Eight logic inputs from front panel/foot switches,
b. Three 8-bit DACs (from said first and second sensors and a generic coupler)
c. Optical encoder inputs from a stepper motor or other actuator.

The operational characteristics and programming sequences of certain embodiments of the control unit (17) in accordance with embodiments can include the following, non-limiting examples:

a. Power up; reset and internal calibration, load lookup tables from ROM.
b. Read: first sensor (22) and second sensor (29), compare to ROM, out put on LCD bar-graph (28) (31). Actuator position. Check all I/O for expected level, set alarm.
c. Close Actuator (22), read generic coupler DAC or gas mixture monitor (15) value, wait 30 seconds and recheck, loop until value in consistent between readings, set alarm after four unsuccessful attempts. Flashing output to display=Check Vaporizer plus audio alarm. Loop until fixed.
d. If step "c" is okay, save DAC value as zero reference level.
e. Check first and second sensors. DAC values should be within power up range stored in ROM. Set alarm if nor in spec. Outputs to LCD bar-graph display.
f. Request anesthetic delivery profile from user: new or stored profile? Monitor switch inputs.
g. Load saved anesthetic delivery profile from RAM.
h. New anesthetic delivery profile: Request time at level a, b, c, d, e, f. User to input duration and level (perhaps up to 6 periods). Save profile. Output audio beep as each level is completed.
i. Check requested values for amount versus time against ROM safety limits. Provide alarm if value exceeded.
j. Check second sensor value against stored profile value if second sensor>ROM then set alarm to warn user that CO2 filter will require changing. Provide over-ride option to user.
k. Request user to press start.
l. Set actuator to select profile value, recheck sensors. Loop to check for compliance on both sensor values and actuator position. Monitor user over-ride interrupt. Store profile values every 30 seconds if user over ride is activated. Set continuous alarm if values to out of range. Output position information to actuator as profile changes.
Provide 3 minute and 1 minute warnings.
m. Of user selects over-ride, translate switch inputs into actuator output. Monitor and provide user alert if safety profiles are exceeded. Store selected values and timing information in long-term memory. Purge first half of long term memory when memory is full or every 30 days.
n. High level interrupts:
1. Stop/start switch
2. Generic coupler DAC output
3. Second Sensor
4. User input pin (logic high level)
o. Timer output: Request user to input duration and start (i.e., end of phase b, start of phase c, start phase d, or the like). Provide output line (logic high) to drive OEM relay, or the like.

Figure 3A:
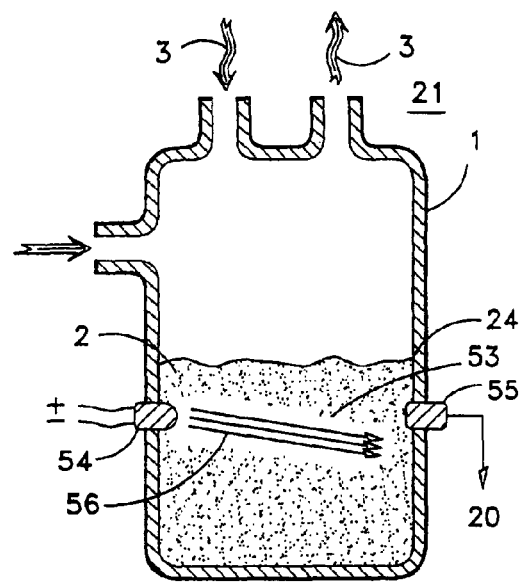
FIG. 3A shows an embodiment of a first sensor having an optical path responsive to the anesthetic in the anesthetic source.
Figure 3B:
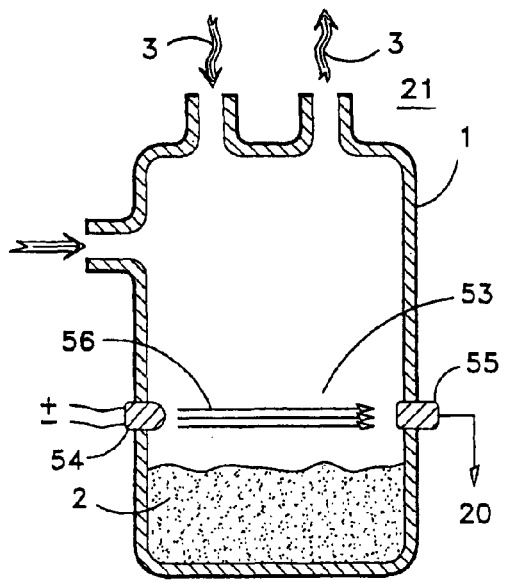
FIG. 3B shows the embodiment of a first sensor as shown in FIG. 3A having an optical path above the level of the anesthetic in the anesthetic source.

Now referring primarily to FIG. 3, the invention can further include as the first sensor (21) an anesthetic sensor which can generate the first signal (20) which corresponds with one or more level(s) of anesthetic (24) in the anesthetic source (1). The signal can be processed by an anesthetic level assessment element (22) further included as a component of controller (18). The controller (18) can further include an anesthetic level indicator (23) which can provide a visual, auditory, or other sensorial perceivable indicia of anesthetic level in the anesthetic source (1). The control unit (18) can further include an alarm element (45) which can generate an audible, visual or other sensorial perceivable indicia when the level of anesthetic (2) in the anesthetic source (1) corresponds to a pre-established level or pre-established delivery rate, or when the level of anesthetic, or the delivery rate of anesthetic deviates from the pre-established, pre-determined or selected level or rate of delivery or deviates from the anesthetic delivery profile (33).

A basic embodiment of the first anesthetic sensor (21) as shown by FIG. 3, locates a single optical path (53) within the anesthetic source (1) between a light source (54), such as a light emitting diode ("LED") or laser, and a light detector (55), such as a as "photo transistor", "photo cell", "photo resistors", "photodiode", or the like. In the absence of any anesthetic (2) in the optical path (53) the emitted light (56) remains incident upon the detector (55) which generates a first sensor signal (20).

A non-limiting example of the detector (55) can be illustrated by a PIN photo detector which behaves very much like a small solar cell to convert light energy into electrical energy. Like solar cells, the PIN photodiode can produce a voltage (about 0.5V) in response to light and can also generate a current proportional to the intensity of the light striking it. However, this unbiased current sourcing mode, or "photovoltaic" mode, is seldom used in through-the-air communications since it is less efficient and is slow in responding to short light flashes. The most common configuration is the "reversed biased" or "photoconductive" scheme. In the reversed biased mode, the PIN detector is biased by an external direct current power supply ranging from a few volts to as high as 50 volts. When biased, the device behaves as a leaky diode whose leakage current is dependent on the intensity of the light striking the device's active area. It is important to note that the intensity of a light source is defined in terms of power, not energy. When detecting infrared light at its 900 nanometer peak response point, a typical PIN diode will leak about one milliamp of current for every two milliwatts of light power striking it (50% efficiency).

However, in the presence of an anesthetic (2) the direction in which the emitted light (56) travels can be bent as shown by FIG. 3A. The amount of bending that takes place depends on the characteristics of the anesthetic (2) and the wavelength of the light (56) being emitted. Most organic based liquids such as anesthetics have refractive indices between 1.45 and 1.55. However, the index of refraction will vary due to the molecular structure of the anesthetic and the way that structure interacts with photons of differing wavelengths as shown by FIG. 6.

Figure 6:
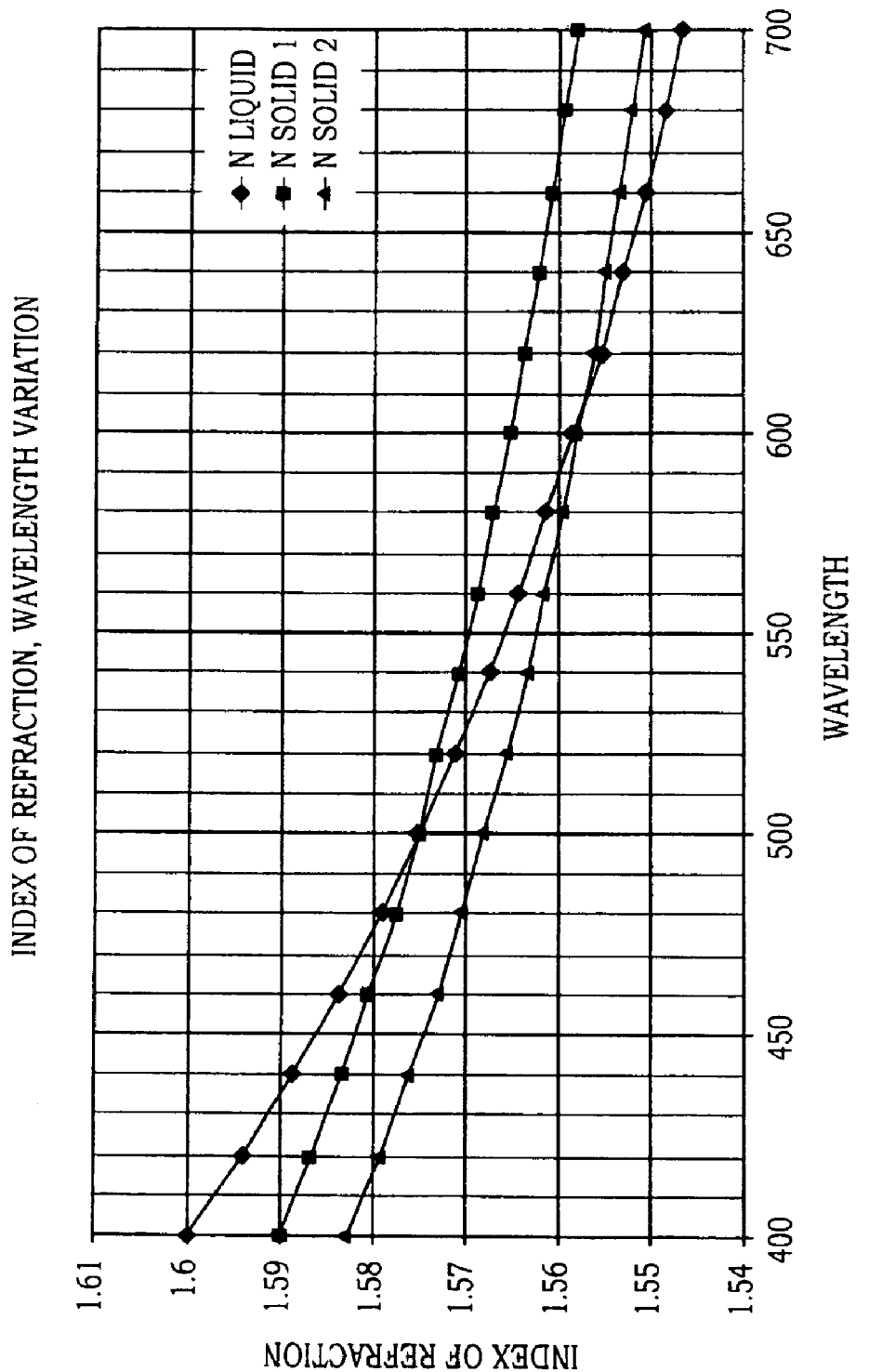
FIG. 6 shows graph which plots index of refraction against wavelength for particular liquids and solids.

As shown in FIG. 6 the index of refraction increases as the wave length of the emitted light decreases. The wavelength of the emitted light in the optical path can be selected to generate a sufficient index of refraction in a particular anesthetic(s) to bend the direction in which the emitted light (56) travels to avoid striking the detector (55).

LED's emit predominantly light of a single color such as red, orange, amber, yellow, green, blue or white as shown by Table 2.

TABLE 2

| Type | Color | Luminous intensity | Viewing angle | Wavelength |
|---|---|---|---|---|
| Standard | Red | 5 mcd @ 10 mA | 60° | 660 nm |
| Standard | Bright red | 80 mcd @ 10 mA | 60° | 625 nm |
| Standard | Yellow | 32 mcd @ 10 mA | 60° | 590 nm |
| Standard | Green | 32 mcd @ 10 mA | 60° | 565 nm |
| High intensity | Blue | 60 mcd @ 20 mA | 50° | 430 nm |
| Super bright | Red | 500 mcd @ 20 mA | 60° | 660 nm |
| Low current | Red | 5 mcd @ 2 mA | 60° | 625 nm |

Figure 3C:
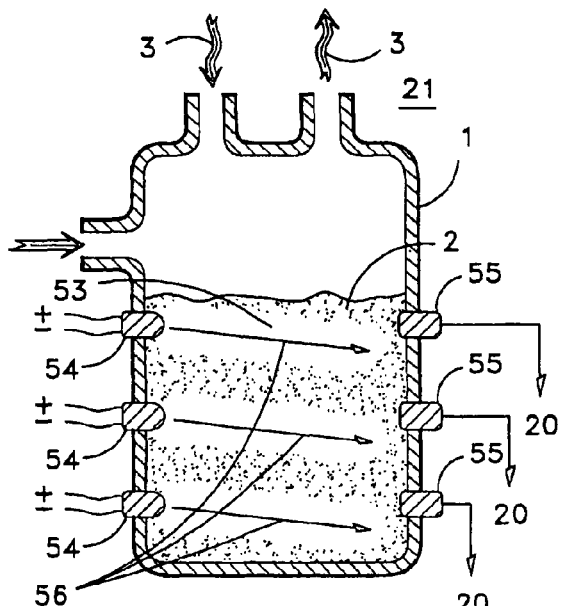
FIG. 3C shows an embodiment a first sensor having a plurality of optical paths for incremental detection of the level of anesthetic in the anesthetic source.

The range in the emitted color of available LEDs allows adjustment of the refractive index of the various anesthetics to generate sufficient bending of the emitted light (56) over the distance of the optical path (53) in the anesthetic source (1), such as a conventional vaporizer, to avoid striking the detector (55) when the anesthetic (2) enters the optical path (53) of the anesthetic sensor (21). By setting the optical path at the desired level in the anesthetic source (1), no signal is produced so long as the level of the anesthetic is above the desired level and a signal is produced if the anesthetic drops below the desired level. The signal (20) generated, or the lack of a signal generated, can be processed by the controller (18) to provide a visual, auditory, or other sensorial perceivable indicia (23) of the anesthetic level (24) in the anesthetic source (1). As shown by FIG. 3C, as to certain embodiments of the invention, a plurality of optical paths can be located within the anesthetic source (1) to provide incremental detection of any change the in anesthetic level (24) in the anesthetic source (1). A particular anesthetic sensor suitable for use in accordance with the invention can be a Frontier Engineering part number VAP-001 which measures the dielectric absorption caused by the presence of a gas or vapor in a calibrated volume. Frontier Engineering, 15541 Weld County Road 33, Platteville, Colo. USA 80651.

Figure 4:
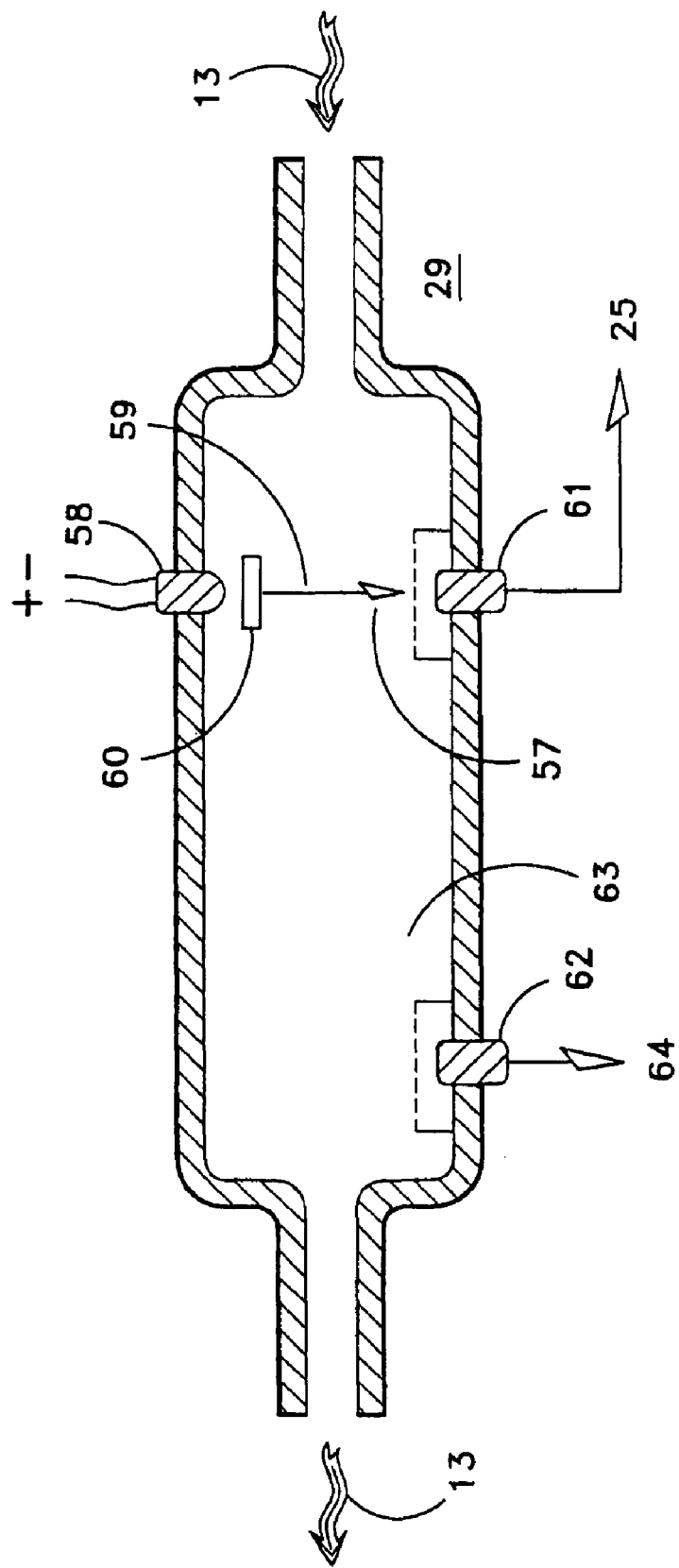
FIG. 4 shows an embodiment of a second sensor responsive to carbon dioxide in the re-breathing circuit.

Now referring primarily to FIG. 4, the invention can further include as the second sensor (26) a carbon dioxide sensor (26) which generates the second sensor signal (25) processed by a carbon dioxide assessment element (27) or second signal processor of control unit (18) to determine the percent, partial pressure, or concentration of carbon dioxide in the mixture of gases in the exhalation circuit (10), either before passing through the carbon dioxide absorber (14) or after passing through the carbon dioxide absorber (15). Certain embodiments of the carbon dioxide sensor (26) passes a portion of the exhaled mixture of gases (13) in the exhalation circuit (12) through an optical path (57) for analysis by a non-dispersive infrared method. As to these embodiments of the invention, the carbon dioxide sensor (26) provides an infrared emission source (58) which emits an amount of infrared radiation (59) characteristic of the carbon dioxide absorption spectra. The infrared emission source can emit a broad band infrared radiation (59) and a band pass filter (60) can be chosen to produce a narrow range of energy frequencies to match a strong absorption band of carbon dioxide (such as about 630 $cm^{-1}$), while avoiding absorption bands from other gases present in the exhalation circuit. The infrared radiation (59) emitted by the infrared emission source (58) travels along the optical path (59) incident to a first infrared detector (61). Any carbon dioxide present in the optical path (59) of the carbon dioxide sensor (26) selectively absorbs a portion of emitted infrared radiation (59). The non-absorbed portion of the emitted infrared radiation (59) incident upon the first infrared detector (61) results in generation of a first infrared signal (25) variably responsive to the infrared radiation (59) incident upon the first infrared detector (61). A second infrared emission detector (62) variably responsive to the amount of background infrared radiation (63) generates a second infrared signal (64). Both the first infrared signal (25) and the second infrared signal (64) are received by a carbon dioxide level determination element (27) which subtracts the second infrared signal from the first infrared signal and processes the resulting signal to determine the percentage, partial pressure, or concentration of carbon dioxide in the exhalation circuit (13). A Frontier Engineering "CO2 IntelliVet" carbon dioxide monitor is suitable for use in certain embodiments of the invention as the second sensor or CO2 sensor. Frontier Engineering, 15541 Weld County Road 33, Platteville, Colo. USA 80651. The CO2 Intellivet carbon dioxide monitor provides an accuracy of about two percent full scale (0%-20% carbon dioxide full scale) with a repeatability of about one percent of full scale.

The controller (18) can further include a carbon dioxide indicator (65) coupled to the carbon dioxide determination element (28). The carbon dioxide indicator (68) can provide sensorial perceivable indicia of the amount of carbon dioxide detected in the exhalation circuit (13) or the inhalation circuit (10) depending on the location of the carbon dioxide sensor (29). The sensorial perceivable indicia can include visual indicia such as gauges, illuminated bar graphs, LED displays, or the like. The audible indicia can include different tones, different decibel levels, different pulse rates, or the like. The controller (18) can further provide an alarm element (65) which generates the audible indicia, visual indicia, or other indicia when the percent carbon dioxide, partial pressure of carbon dioxide, or concentration of carbon dioxide, reaches a certain threshold level in the exhalation circuit (13) or the inhalation circuit (10) depending on the location of the carbon dioxide sensor (29).

As to certain embodiments of the invention, the carbon dioxide determination element (27) can be coupled to a signal controlled oxygen flow regulator (66) to assure sufficient partial pressures of oxygen to the patient (11) in the inhalation circuit (10). As to other embodiments of the invention the carbon dioxide determination element (27) can coupled to a carbon dioxide absorbent replacement indicator (67) activated when a selected threshold level of carbon dioxide in the mixture of gases passing from the carbon dioxide absorber (14) is detected.

Figure 5:
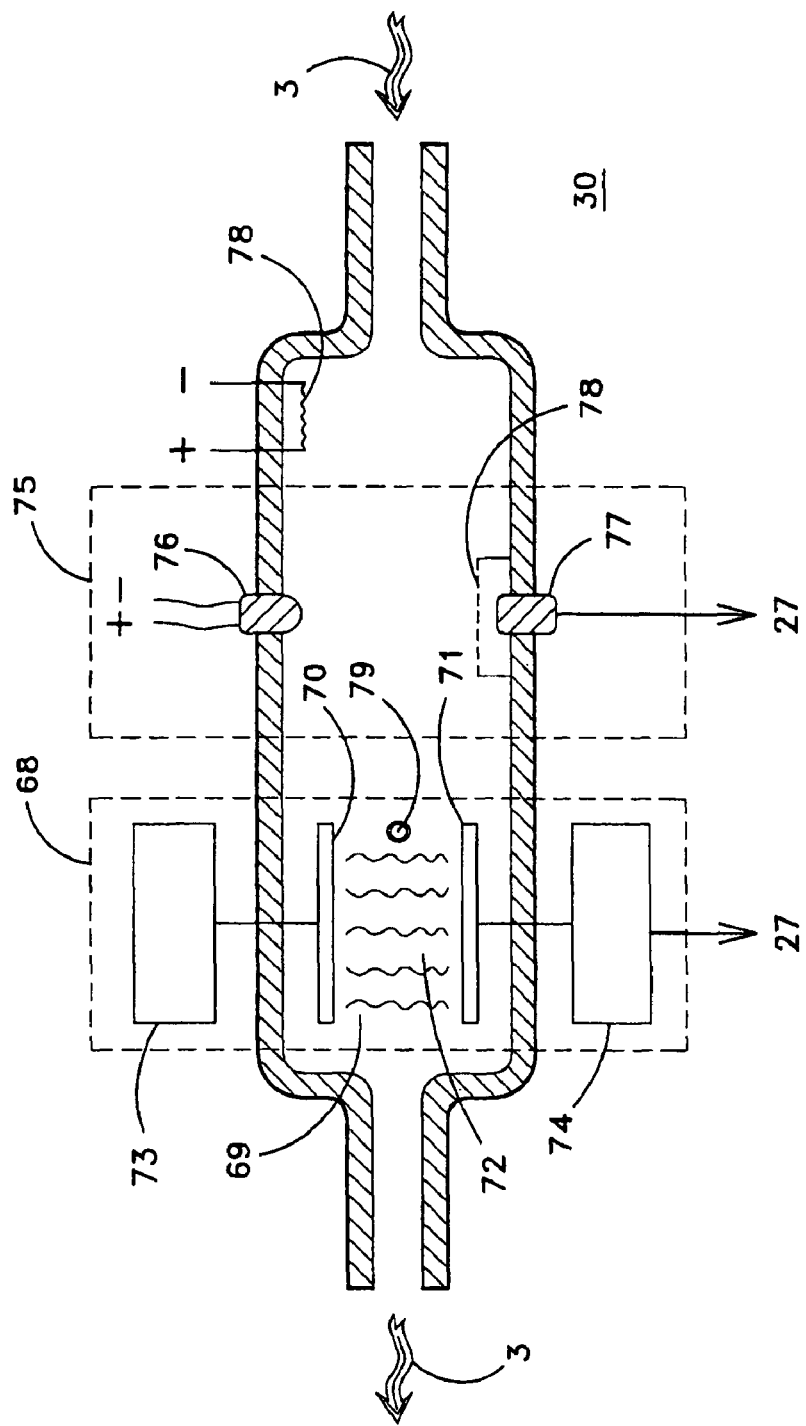
FIG. 5 shows and embodiment of a third sensor responsive to the type or kind of anesthetic in the re-breathing circuit.

Now referring primarily to FIG. 5, the invention can further include as the third sensor (30), a gas-vapor sensor, which generates the third sensor signal(s) (27) processed by the third signal processor (31), an anesthetic gas analysis element, of the controller (18). The gas-vapor sensor (30) can include a radio frequency coupler (68). The radio frequency coupler (68) measures the dielectric absorption caused by the presence of a gas (3) or vapor in a calibrated volume (69) at a specific temperature. A temperature sensor (79) can be used to provide a temperature signal to the anesthetic gas analysis element so that the temperature of the gas mixture in the gas-vapor sensor can be determined by the anesthetic gas analysis element of the controller (18). A stable radio frequency ("RF") (72) can be generated between a first plate (70) and a second plate (71) of the radio frequency coupler (68) by utilizing a high frequency oscillator (73) connected to the first plate (70) to generate an electromagnetic field which propagates through the space between the first plate (70) and the second plate (71). The radiofrequency detector (74) connected to the second plate (71) generates a voltage depending upon the strength of the electromagnetic field reaching the second plate (71) from the first plate (70). When a gas (3) flows between the first plate (70) and the second plate (71), the amount of energy reaching the second plate (71) is reduced by the dielectric absorption of the gas (3). In an electromagnetic field, the centers of the nonpolar molecules of a dielectric are displaced, and the polar molecules become oriented close to the field. The net effect is the appearance of charges at the boundaries of the dielectric. The frictional work done in orientation absorbs energy from the field which appears as heat and a loss of energy at the second plate (71). Depending upon the anesthetics (2) utilized for the inhalation anesthesia the proper radio frequency can be generated by the oscillator (73) to achieve a measurable absorption of the RF field. With a controlled volume and temperature and a known flow rate of the anesthetic (2), the measured absorption can be used to identify the anesthetic in the flow of gas. An anesthetic flow rate detector (75) which provides an infrared source (76) and an infrared detector (77) as discussed above can be utilized to determine the concentration of the anesthetic in the gas flow prior to introduction into the radio frequency coupler (68). A heating element precedes the anesthetic flow rate detector (75) to insure that the anesthetic gas/vapor is boiled away at a controlled rate in conjunction with the temperature sensor (79)). This provides assurance that a blockage does not exist within the flow path. Otherwise, the anesthetic flow rate detector may not detect that flow rate has terminated.

A particular gas-vapor sensor suitable for use in accordance with the invention can be a Frontier Engineering GA-001 which measures the dielectric absorption caused by the presence of a gas or vapor in a calibrated volume. Frontier Engineering, 15541 Weld County Road 33, Platteville, Colo. USA 80651.

As can be easily understood from the foregoing, the basic concepts of the present invention may be embodied in a variety of ways. The invention involves numerous and varied embodiments of a veterinary anesthesia monitor system and methods of making and using such veterinary anesthesia monitor system.

As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "sensor" should be understood to encompass disclosure of the act of "sensing"—whether explicitly discussed or not—and, conversely, were there effectively disclosure of the act of "sensing", such a disclosure should be understood to encompass disclosure of a "sensor" and even a "means for sensing." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Webster's Unabridged Dictionary, second edition, each definition hereby incorporated by reference.

Thus, the applicant(s) should be understood to claim at least: i) each of the anesthesia monitor devices herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. An anesthesia device, comprising:
   a. an anesthetic source which contains an amount of anesthetic;
   b. a flow of gas through said anesthetic source which entrains an amount of said anesthetic;
   c. an inhalation circuit coupled to said anesthetic source which provides a flow path to deliver said anesthetic entrained in said flow of gas to a patient;
   d. an exhalation circuit in which an exhaled mixture of gases of said patient flow;
   e. a carbon dioxide absorber containing a carbon dioxide absorbent which receives said exhaled mixture of gases of said patient;
   f. a carbon dioxide sensor responsive to an amount of carbon dioxide in said flow of gas delivered to said patient, wherein said carbon dioxide sensor comprises:

i. an infrared emission source which generates an amount of infrared radiation passed through said flow of gases delivered to said patient;
ii. an infrared emission detector which detects said amount of infrared radiation after said amount of infrared radiation passes through said flow of gases delivered to said patient;
iii. an infrared signal generator which generates a infrared signal in response to detection of said amount of infrared radiation after said amount of infrared radiation passes through said flow of gases delivered to said patient; and
iv. an infrared signal receiver which receives said infrared signal;
g. a carbon dioxide level determination element coupled to said infrared signal receiver which determines an amount of carbon dioxide in said flow of gases delivered to said patient;
h. a gas-vapor sensor having a radio frequency coupler which includes an oscillator coupled to a first plate and radiofrequency detector coupled to a second plate, said oscillator generating an electromagnetic field between said first plate and said second plate, said radiofrequency detector generating a signal which varies based upon said amount of anesthetic in said flow of gas between said first plate and said second plate; and
i. a gas analysis element coupled to said gas-vapor sensor which identifies a type of anesthetic in said flow of gas.

2. An anesthesia device as described in claim 1, wherein said anesthetic source which contains said amount of anesthetic comprises an anesthetic vaporizer, and wherein a flow of gas through said anesthetic vaporizer entrains an amount of said anesthetic.

3. An anesthesia device as described in claim 2, wherein said flow of gas comprises a flow of gas selected from the group consisting of: oxygen, a mixture of gases, and a mixture of partial pressures of gases containing oxygen.

4. An anesthesia device as described in claim 3, further comprising a gas flow regulator which adjusts said flow of gas through said anesthetic vaporizer.

5. An anesthesia device as described in claim 4, where in said gas flow regulator responds to said anesthetic delivery rate adjustment element to adjust said rate of delivery of said amount of anesthetic from said anesthetic source to said predetermined rate of delivery of said amount of anesthetic.

6. An anesthesia device as described in claim 5, further comprising a heater element which maintains said anesthetic contained by said vaporizer at a temperature.

7. An anesthesia device as described in claim 6, further comprising a controller which provides at least one anesthesia profile, wherein said at least one anesthesia profile establishes said predetermined rate of delivery of said amount of anesthetic delivery within each of a plurality of time periods.

8. An anesthesia device as described in claim 7, wherein said at least one anesthesia delivery profile comprises a plurality of anesthesia delivery profiles, and wherein said controller further comprises an anesthesia profile selection element which allows selection, of one each anesthesia profile from said plurality of anesthetic delivery profiles.

9. An anesthesia device as described in claim 8, wherein said controller further comprises an anesthesia profile generation element comprising:
a. a time period selection element which allows said user to establish the beginning and the end of each of said plurality of time periods; and
b. a anesthetic delivery rate selection element which allows said user to establish said predetermined rate of delivery of said amount of anesthetic within said time period.

10. An anesthesia device as described in claim 9, a carbon dioxide level indicator coupled to said carbon dioxide level determination element which provides sensorially perceivable indicia which correspond to said amount of carbon dioxide in said flow of gas delivered to said patient.

11. An anesthesia device as described in claim 10, wherein said sensorially perceivable indicia are selected from the group consisting of: an emitted light, an audible sound, an illuminated display and a liquid crystal display.

12. An anesthesia device as described in claim 11, wherein said anesthetic comprises an anesthetic selected from the group consisting of: Halothane, Enflurane, Isoflurane, Desflurane, or Sevflurane.

13. An anesthesia device as described in claim 12, wherein said patient comprises an animal selected from the group consisting of: a human, an animal, a dog, a cat, a rat, a guinea pig, a horse, and a donkey.

* * * * *